US008091553B2

(12) United States Patent
Bordewick et al.

(10) Patent No.: US 8,091,553 B2
(45) Date of Patent: *Jan. 10, 2012

(54) FACE MASK SUPPORT

(75) Inventors: Steven S. Bordewick, North Shoreview, MN (US); David Markovich, Eden Prairie, MN (US); Laurel D. Brandt, Eagan, MN (US); Mark J. Weimholt, Coon Rapids, MN (US); Amy Raatikka, Maple Grove, MN (US)

(73) Assignee: Somnetics Global Pte. Ltd., Singapore (SG)

( * ) Notice: Subject to any disclaimer, the term of this patent is extended or adjusted under 35 U.S.C. 154(b) by 502 days.

This patent is subject to a terminal disclaimer.

(21) Appl. No.: 11/455,544

(22) Filed: Jun. 19, 2006

(65) Prior Publication Data
US 2006/0231102 A1 Oct. 19, 2006

Related U.S. Application Data

(63) Continuation of application No. 11/056,858, filed on Feb. 12, 2005, now Pat. No. 7,089,941, which is a continuation-in-part of application No. 10/643,642, filed on Aug. 19, 2003, now Pat. No. 6,854,465.

(60) Provisional application No. 60/619,539, filed on Oct. 15, 2004, provisional application No. 60/404,685, filed on Aug. 20, 2002.

(51) Int. Cl.
*A62B 18/08* (2006.01)
*A62B 18/02* (2006.01)
*A62B 7/10* (2006.01)
*A62B 17/04* (2006.01)
*A61M 16/00* (2006.01)
*A41D 13/00* (2006.01)
*A42B 1/06* (2006.01)
*A42B 3/00* (2006.01)

(52) U.S. Cl. ......... 128/207.11; 128/207.13; 128/207.17; 128/205.25; 128/206.12; 128/206.18; 128/206.21; 128/206.27; 128/206.28; 128/201.22; 128/201.23; 128/201.24; 2/5; 2/9; 2/410

(58) Field of Classification Search ............. 128/207.11, 128/207.13, 207.17, 205.25, 206.12, 206.18, 128/206.21, 206.27, 206.28, 201.22, 201.23, 128/201.24; 2/410, 5, 6.1, 6.2, 6.6, 6.8, 417, 2/418, 421, 422, 424, 9, 171, 173, 202, 205, 2/206, 209, 908, 909, 912
See application file for complete search history.

(56) References Cited

U.S. PATENT DOCUMENTS 1,081,745 A 12/1913 Johnston et al.
(Continued)

FOREIGN PATENT DOCUMENTS

EP 0 549 299 A2 6/1993
(Continued)

*Primary Examiner* — Patricia Bianco
*Assistant Examiner* — Nihir Patel
(74) *Attorney, Agent, or Firm* — Mueting, Raasch & Gebhardt, P.A.

(57) ABSTRACT

A face mask support for continuous positive airway pressure comprises a circumferential band with biasing means support at the crown of the head on the medial line of the head. The circumferential edge of the cap extends from just below the forehead of a patient to below the inion protrusion at the nape of the neck. A biasing means which is preferably of length of spring steel is formed so as to extend from the biasing means support hold a nasal or face mask apposed to the face of a patient. The circumferential band is stabilized by a band extending from the circumferential band at the region of the ear to the biasing means support.

5 Claims, 13 Drawing Sheets

U.S. PATENT DOCUMENTS

| | | | |
|---|---|---|---|
| 1,282,527 A | 10/1918 | Bidonde |
| 1,632,449 A | 6/1927 | McKesson |
| 2,241,535 A | 5/1941 | Boothby et al. |
| 2,965,902 A | 12/1960 | Louch |
| 3,599,635 A | 8/1971 | Ansite |
| 3,721,233 A | 3/1973 | Montgomery et al. |
| 3,799,164 A | 3/1974 | Rollins |
| 4,151,843 A | 5/1979 | Brekke et al. |
| 4,593,688 A | 6/1986 | Payton |
| 4,644,947 A | 2/1987 | Whitwam et al. |
| 4,944,310 A | 7/1990 | Sullivan |
| 5,054,484 A | 10/1991 | Hebeler, Jr. |
| 5,421,799 A | 6/1995 | Rabin et al. |
| 5,538,000 A | 7/1996 | Rudolph |
| 5,542,128 A | 8/1996 | Lomas |
| 5,542,129 A | 8/1996 | Lomas |
| 5,623,923 A | 4/1997 | Bertheau et al. |
| 5,662,101 A | 9/1997 | Ogden et al. |
| 5,687,715 A | 11/1997 | Landis et al. |
| 5,724,965 A | 3/1998 | Handke et al. |
| 5,954,050 A | 9/1999 | Christopher |
| 6,119,693 A | 9/2000 | Kwok et al. |
| 6,347,631 B1 | 2/2002 | Hansen et al. |
| 6,494,207 B1 | 12/2002 | Kwok |
| 6,505,623 B1 | 1/2003 | Hansen |
| 6,516,802 B2 | 2/2003 | Hansen et al. |
| 6,530,373 B1 | 3/2003 | Patron et al. |
| 6,532,960 B1 | 3/2003 | Yurko |
| 6,536,435 B1 | 3/2003 | Fecteau et al. |
| 6,694,978 B1 | 2/2004 | Bennarsten |
| 6,789,543 B2 | 9/2004 | Cannon |
| 6,854,465 B2 * | 2/2005 | Bordewick et al. ...... 128/207.11 |
| 6,886,564 B2 | 5/2005 | Sullivan et al. |
| 7,089,941 B2 * | 8/2006 | Bordewick et al. ...... 128/207.11 |
| 7,156,090 B2 | 1/2007 | Nomori |
| 7,357,136 B2 * | 4/2008 | Ho et al. .................. 128/207.11 |
| 7,487,778 B2 | 2/2009 | Freitag |
| 7,588,033 B2 | 9/2009 | Wondka |
| 7,845,353 B2 | 12/2010 | Bordewick et al. |
| 2002/0011248 A1 | 1/2002 | Hansen et al. |
| 2003/0051732 A1 | 3/2003 | Smith et al. |
| 2003/0172936 A1 | 9/2003 | Wilkie et al. |
| 2004/0025882 A1 | 2/2004 | Madaus et al. |
| 2004/0035427 A1 | 2/2004 | Bordewick et al. |
| 2004/0226562 A1 | 11/2004 | Bordewick |
| 2004/0226566 A1 | 11/2004 | Gunaratnam et al. |
| 2005/0076913 A1 | 4/2005 | Ho et al. |
| 2006/0231097 A1 | 10/2006 | Dougherty et al. |
| 2007/0277825 A1 | 12/2007 | Bordewick et al. |
| 2007/0277827 A1 | 12/2007 | Bordewick et al. |
| 2008/0006275 A1 | 1/2008 | Nickelson et al. |

FOREIGN PATENT DOCUMENTS

| | | |
|---|---|---|
| EP | 0 549 299 A3 | 10/1993 |
| EP | 1334742 A2 | 3/2004 |
| WO | WO 98/48878 A2 | 11/1998 |
| WO | WO 2004012803 A1 | 2/2004 |
| WO | WO 2006/044120 A2 | 4/2006 |

* cited by examiner

FACE MASK SUPPORT

CROSS REFERENCE TO RELATED APPLICATIONS

The present Utility Patent Application is a continuation of commonly assigned U.S. patent application Ser. No. 11/056,858 filed Feb. 12, 2005 now U.S. Pat. No. 7,089,941, which claims priority from U.S. Provisional Application No. 60/619,539 filed on Oct. 15, 2004 and which is a continuation-in-part of U.S. application Ser. No. 10/643,642, now U.S. Pat. No. 6,854,465 filed on Aug. 19, 2003, which claims priority from U.S. Provisional Application No. 60/404,685, filed Aug. 20, 2002, the disclosures of which are hereby incorporated by reference in their entirety.

FIELD OF THE INVENTION

This invention relates generally to a face mask support for providing pressurized gas to a patient. The mask support may be connected to a full face mask or a nasal mask. The pressurized gas may be ambient air, oxygen or a mixture thereof.

BACKGROUND OF THE INVENTION

As a person ages, airway patency may be reduced due to loss of muscle tone in the muscles of the throat which normally serve to prevent the tissues from impinging on the airway. This condition is more severe in patients who are obese, have naturally narrow airways or airways that may be partially blocked by tonsils, soft palate or uvula. The result can be snoring as the tissues vibrate as air is forced through the narrowed airway under heightened pressure. Snoring is disruptive to sleep; the snorer not only keeps companions awake but will himself awaken many times in the night. This sleep disturbance leads to a feeling of tiredness or exhaustion during the day and a decrease in mental and physical performance.

In about a third of snorers, the condition can be lethal. When narrowing of the airway proceeds to complete occlusion, the condition is termed sleep apnea. A faulty feedback loop between the brain and the respiratory system lets the airway completely collapse until the brain registers low oxygen levels and the patient jerks awake to resume breathing. These constant jump starts, which can happen as often as once a minute, send the heart rate on a roller coaster. In susceptible patients, high heart rates can bring on fatal arrhythmia or myocardial infarction.

Continuous positive airway pressure (CPAP) is a method in use for some time to alleviate the symptoms of snoring or sleep apnea by delivering air or gas under a pressure sufficient to mimic the effect of the natural waking tone of the throat muscles in holding the soft tissues around the airway from partially or totally occluding the airway passage. Patients other than those with airway problems can benefit from CPAP. These groups include patients with weakened respiratory muscles who cannot pull air into their lungs, such as those with post polio or amyotrophic lateral sclerosis disease, patients with traumatic nerve damage or adult respiratory distress. CPAP apparatus are generally comprised of a blower for providing a stream of air or gas under pressure, a mask and tubing to connect the mask to the blower source. The mask can cover both the mouth and nose, the nose alone, or have plugs that insert only into the nares. Whatever the configuration, the mask must have, as a minimum, a means of sealing the mask to the face so that the blower gas does not escape, thereby reducing the pressure to the airway. Vents must be provided for exhaled gases. Preferably the vents are placed so as to avoid the eyes of the patient. A mask support is necessary to hold the mask and tubing in proper apposition.

Patient compliance is often a problem. Many of the masks currently available are uncomfortable, tend to be dislodged during sleep or disconnected from the blower source. If the mask is a full face mask covering both nose and mouth or a nasal mask covering only the nose, the peripheries of the mask will touch the bridge of the nose, the upper or lower lip and must seal around the malar region. Individual variations in the topography, especially of the malar region, make it necessary to hold the mask to the face with some pressure. It has been shown that a double seal, with a semirigid internal support and a flexible skirt can be inflated with air, forming a seal that more readily conforms to the malar region. The ideal mask support is usable with any variety of full face or nasal mask to accommodate individual needs and preferences.

The mask support must be capable of holding the mask firmly in position with as low a pressure as possible to avoid irritation of the face, especially the bridge of the nose. A popular design comprises a rigid band cantilevered over the medial line of the skull, with the blower source tubing arranged and secured along the band. (U.S. Pat. Nos. 1,081,745 and 6,347,631.) The only points at which the support applies pressure to the patient are at the occipital lobe and the mask.

The need remains for a face mask support that is comfortable, does not apply pressure to small or sensitive areas of the head and is not easily dislodged or disconnected from its blower source.

SUMMARY OF THE INVENTION

A mask support for continuous positive airway pressure comprising a flexible cap and a blower source operably attached to the cap, the blower source being operably attached to a mask. The blower source is preferably a blower unit with external coil-supported, smooth interior tubing connecting the blower to the mask. The lower circumferential edge of the cap surrounds the head from below the inion protrusion of the occipital bone to a point on the medial line of the head defined by a diameter through the head from the occipital lobe to the forehead.

The cap is approximately hemispheric and is made of light, flexible material. The circumferential edge is provided with a means for tightening. The means can be elastic inserts, buckles, draw strings or the like or the entire assembly may be constructed of an elastic material. The medial line from occipital lobe to forehead is reinforced with a flexible but firm band.

The open cap embodiment is comprised of a band defining the circumferential edge and a medial band passing over the approximate medial line of the head and attaching to the circumferential band at the forehead and below the inion protrusion of the occipital bone. The circumferential band is preferably provided with means for adjustment. The medial band may be bifurcated above its attachment to the back of the circumferential band. When the medial band is bifurcated, each arm is separately connected to the circumferential band, close to the medial line. The circumferential and medial bands may be formed from a single piece of material.

The medial band is fitted with a biasing means support that extends from just above the forehead attachment of the circumferential and medial bands back along the medial band to a point near the apex of the cranium. The biasing means support is approximately wedge shaped with the base curved to accommodate the curvature of the cranium and the top surface is at approximately a right angle to the vertical plane of the face and is comprised of a rigid or semi-rigid material so as to afford stable positioning for the biasing means. The biasing means support comprises at least one slot for the insertion of the ends of the biasing means.

The biasing means is comprised of spring steel, springs, or any metallic or plastic capable of transmitting force from one site to another, without fatigue. The biasing means is preferably a continuous length of spring steel formed into a loop and two equal length lateral arms, each end of which is insertible into the biasing means support, parallel to the top surface of the biasing means support and curved to an approximately 90 degree angle with the vertical plane of the face. The biasing means extends thus for a length sufficient to extend forward of the nose, and is at that point formed into a 90 degree curve so as to be parallel to the vertical plane of the face. The descending lateral arms form a loop that fits around the distal surface of the face mask. The mask support is adaptable to hold any full face or nasal mask in place. The descending lateral arms may also be separate length of spring steel, each independently inserted into biasing means and into the face mask at either its proximal or distal end.

The slots of the biasing means support are provided with means for adjusting the length of insertion of the ends of the arms of the biasing means, thereby adjusting the horizontal forward length of the biasing means. The adjustment means may be a ratchet or friction hold. This adjustment accommodates both individual facial differences and the force to be applied to hold the face mask in position.

The circumferential band of the open cap is adjustable at each side of the head, the adjustment being by velcro, buckle, snap clamp or the like. Minor and quick adjustment may be provided by a cord with a slip clamp, which may be quickly pulled and released for minor adjustment and quick sizing. The medial band may likewise be provided with means for adjustment at the back of the head. When the medial band is bifurcated, each arm of the bifurcation may be provided with means for adjustment.

A second embodiment comprises a circumferential band, a stabilizing band, and a biasing means anchored by a biasing means support. This embodiment lacks a medial band. The circumferential band encircles the head from below the inion protrusion of the occipital bone of a patient to a point high on the forehead just below the hair line of a patient. The circumferential band is formed from a flexible material into a semi-rigid outer substrate and an inner substrate of a soft material, which is in contact with the skin or hair of a patient.

The circumferential band is provided with a means for tightening. The means can be Velcro, elastic inserts, buckles, draw strings or the like. The means may be incorporated into a band that is securely attached to the circumferential band by any means, such as ultrasonic welding or glue. The circumferential band is curved into an S-shape at an area just above the ears of a patient.

The stabilizing band extends across the crown of the head and attaches to the circumferential band at each side at approximately the S-shaped curve. The stabilizing band may pass under the biasing means support or may be separately attached to the biasing means support. The attachment may be by any means, such as ultrasonic welding or glue. Preferably, the biasing means support is provided with a loop at each side and the stabilizing band is attached through the loops by buckles, or is turned through the loops back on itself and secured with Velcro.

The biasing means support is approximately wedge shaped with the base curved to accommodate the curvature of the cranium and is comprised of a rigid or semi-rigid material so as to afford stable positioning for the biasing means. The biasing means support extends toward the crown of the head from the forehead area just below the hairline of a patient and the frontmost end is firmly attached to the circumferential band at the forehead and the back end is attached to the stabilizing band. The biasing means support is preferably provided with a cushion lining which is textured so as to allow some air circulation under the support.

The biasing means support comprises at least one slot for the insertion of an end of the biasing means. The circumferential band may have an upward extension from the forehead area to the crown of the head to act as a cushion to the biasing means support. Alternatively, the stabilizing band may extend continuously across the crown of the head and the biasing means may be positioned on the circumferential band in front and directly on the stabilizing band at the crown of the head, wherein the circumferential and stabilizing bands act as cushions.

The biasing means is comprised of spring steel, springs, or any metallic or plastic capable of transmitting force from one site to another, without fatigue. The biasing means may be formed in several configurations, the end or ends of which are insertible into receiving slots on the biasing means support, parallel to the top surface of the biasing means support. The biasing means extends for a horizontal length sufficient to extend forward of the nose, and is at that point formed into a 90-degree curve so as to be parallel to the vertical plane of the face. The descending lateral arm or arms fit around or above the mask. The mask support is adaptable to hold any full face or nasal mask in place.

In any configuration of the biasing means, the horizontal length of the biasing means is fitted with a mechanism for horizontal positioning within the biasing means support so as to adjust the mask support outward from the face. Likewise, the descending arms or arm is fitted with a mechanism for positioning the plenum so as to adjust the mask vertically. The preferred means of adjustment is a ratchet, with the corresponding ratchet fitted into the biasing means support and plenum, respectively.

When the face mask is a full face mask, the biasing means is attached at or around the distal end of the face mask. When the face mask is a nasal mask, the biasing means is attached at or above the nasal mask. Preferably, the face mask support to be used with a nasal mask will incorporate a plenum, a connection means to interface between an air hose and the nasal mask, and at least one hole or preferably several vent holes for exhaled gas. The vent holes are preferably placed at the top surface of the plenum so as to direct the exhaled air away from the patient.

In either embodiment, the mask support is made of soft, flexible material, while the biasing means support is a more rigid material and the biasing means is a very firm material. Preferably, the circumferential band and the stabilizing bands are comprised of two layers of substrate. The outer substrate is sufficiently firm to prevent the band from rolling while the inner substrate, which is in contact with a patient's skin, hair and scalp, is soft and may be provided with texture such as rounded protuberances to allow some air circulation under the support.

When the mask support is made of an elastic material, the means for adjustment may be eliminated. One skilled in the art can readily substitute materials to achieve the same or substantially the same support. Such materials are considered to be within the scope of the appended claims.

BRIEF DESCRIPTION OF THE DRAWINGS

FIG. 8 is an exploded view of the molded bands.

DETAILED DESCRIPTION OF THE INVENTION

When used in this patent application, the following terms have the following meaning:

"Air" is used to denote a gas to be delivered to a patient and includes atmospheric gas, oxygen or a combination thereof.

"Crown of the head" refers to the area of the head past the vertical plane of the forehead, that is, the top of the head.

"Hair line" refers to highest area of the forehead, whether or not hair is present.

"Face mask or full face mask" refers to a mask that covers the nose of a patient and is apposed to the face all around the periphery of the mask.

"Nasal mask" refers to a mask that is apposed to a patient only at the nares.

"Appose" means to press one surface against another.

The objective of the inventors is to provide as lightweight, comfortable CPAP mask support as is consistent with stability. The mask support face mask for CPAP must be held apposed to the face with sufficient force to provide a seal so that the air pressure may be applied directly to the patient's airway without leaking significantly. The force may be through straps or through a biasing means as described in co-pending patent application Ser. No. 10/643,642, the teachings of which are incorporated by reference.

For the purpose of defining this invention, "face mask" or "mask" is used to include any device for linking a positive pressure system (blower) to the airway of a patient. A face mask may be a mask that covers the full face, a mask that covers nose and mouth, a mask that covers only the nose or nasal plugs. A face mask support is any device that holds the face mask apposed to the face.

EXAMPLE 1

First Embodiment

Figure 1:
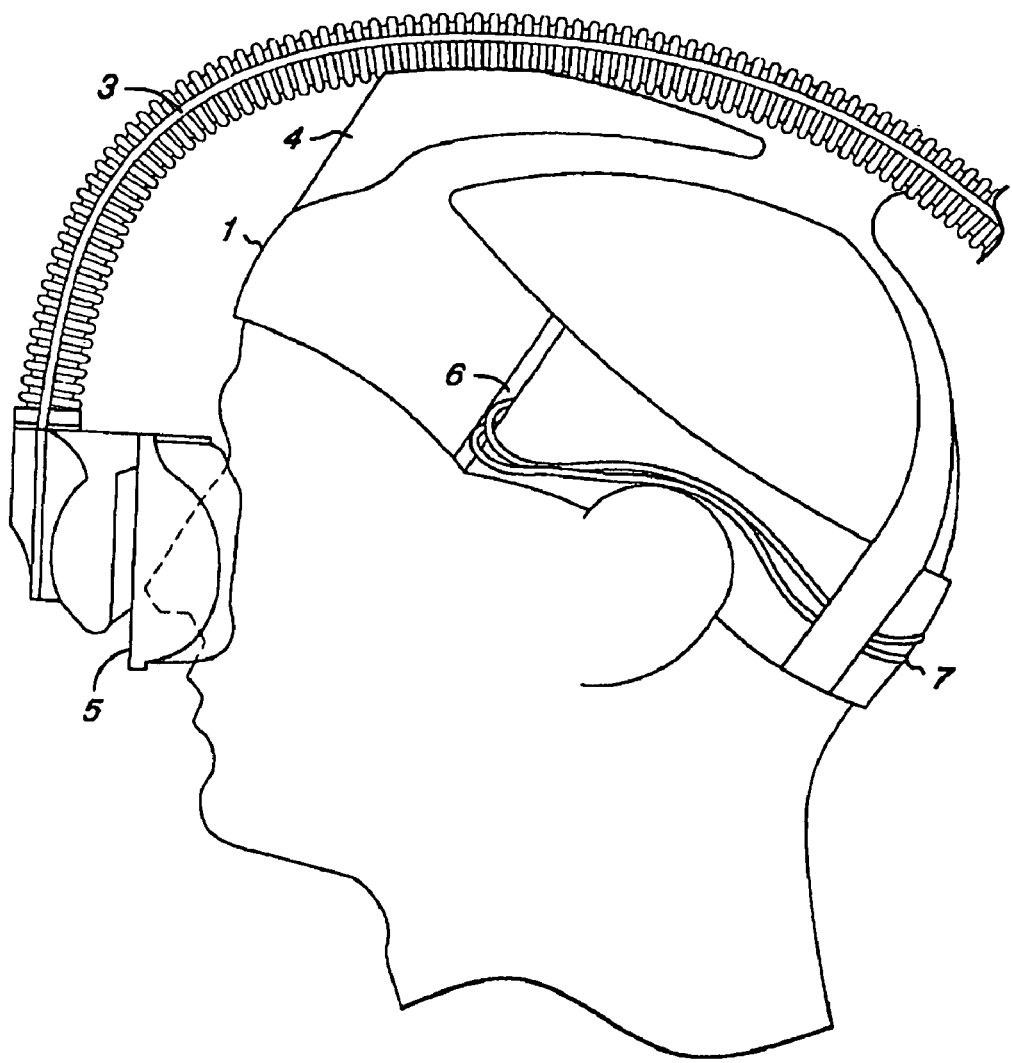
FIG. 1 shows a profile view of the open cap mask support of the invention.

Looking at FIG. 1, the circumference edge 1 of the open cap is seen to extend from the middle of the forehead, avoiding the sensitive eye and eyebrow regions, to below the inion protrusion of the occipital bone (the nape of the neck). The circumferential edge of either the open cap or the closed cap describes a hemisphere. This natural positioning gives stability to the mask support cap, in that the nape, where the spine joins the head, is the "low point" of the head, to which any encircling band will incline to rest. Thus, the circumferential band replaces both the forehead and occipital anchor points that are commonly found on similar devices. (See, e.g., U.S. Pat. No. 6,515,802.) The circumferential band is maintained on the head with loading that is applied independent of the loading of the face seal, unlike the supports in U.S. Patent Application U.S. No. 2002/0117177. The edge of the circumferential band 1 is joined at the forehead and the rear of the head to the medial band 2. Because the headband is sufficiently clamped, the medial band is sufficiently established such that it serves as a stable support for the biasing means support. With the medial band established on the medial line of the head, the biasing means is capable of creating a counter-clockwise moment needed to keep the mask apposed to the face, which translates the force into a clockwise moment of the mask loading force, tending to keep the mask on the face without leaking. The two arms of the biasing means 3 are inserted into the rigid or semi-rigid biasing means support 4 and are looped around the face mask 5. The circumferential band 1 is fitted with adjustment means 6 and quick-sizing cord 7.

Figure 2:
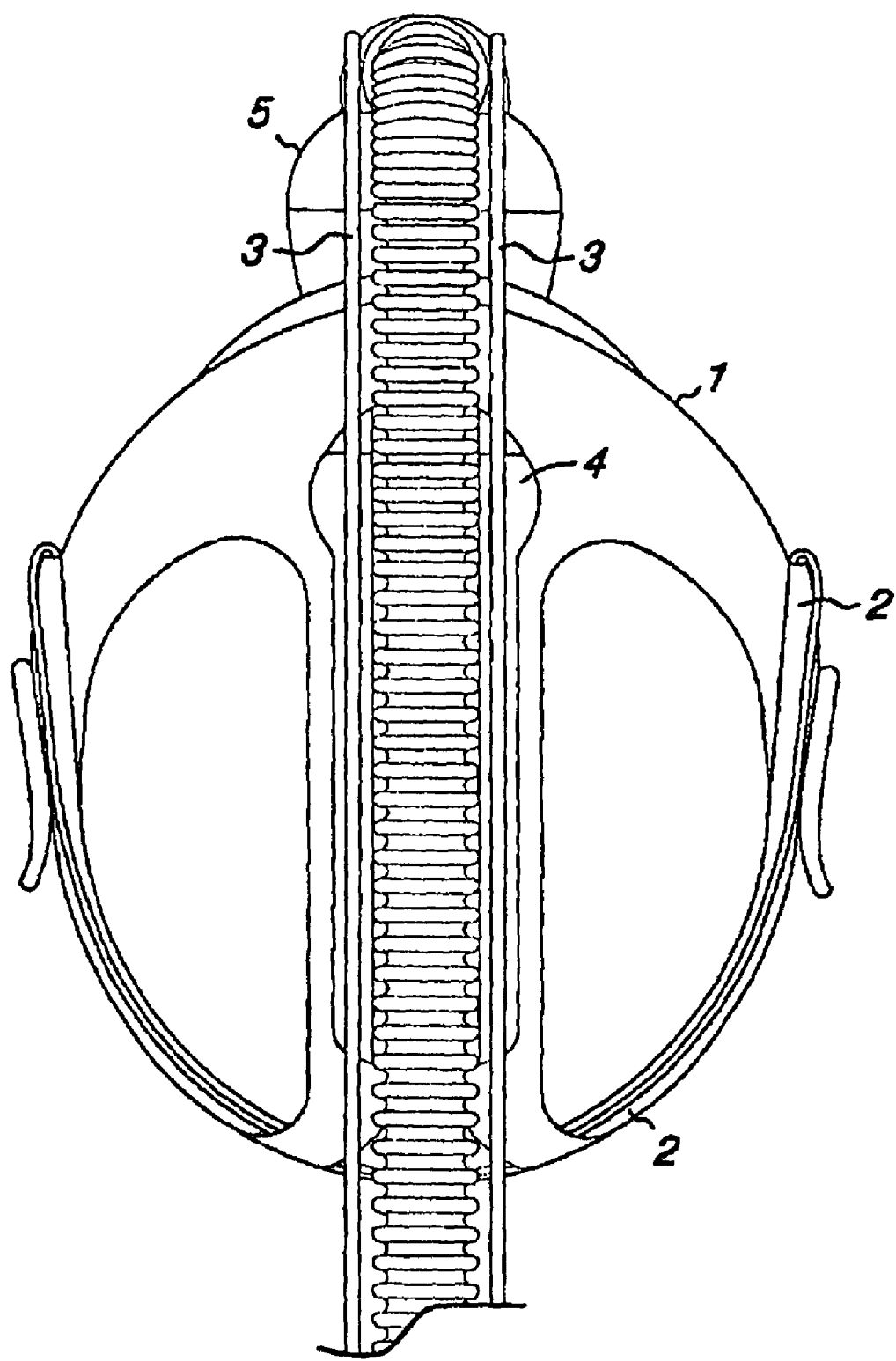
FIG. 2 shows a top view of the mask support of the invention.

Looking at FIG. 2, the circumferential band 1 is seen to extend from the middle of the forehead, avoiding the sensitive eye and eyebrow regions, to below the inion protrusion of the occipital bone (the nape of the neck). This natural positioning gives stability to the mask support cap, in that the nape, where the spine joins the head, is the "low point" of the head, to which any encircling band will incline to rest. The circumferential band 1 is joined at the forehead and the rear of the head to the medial band 2. The two arms of the biasing means 3 are inserted into the rigid or semi-rigid biasing means support 4 and are looped around the face mask 5.

Figure 3:
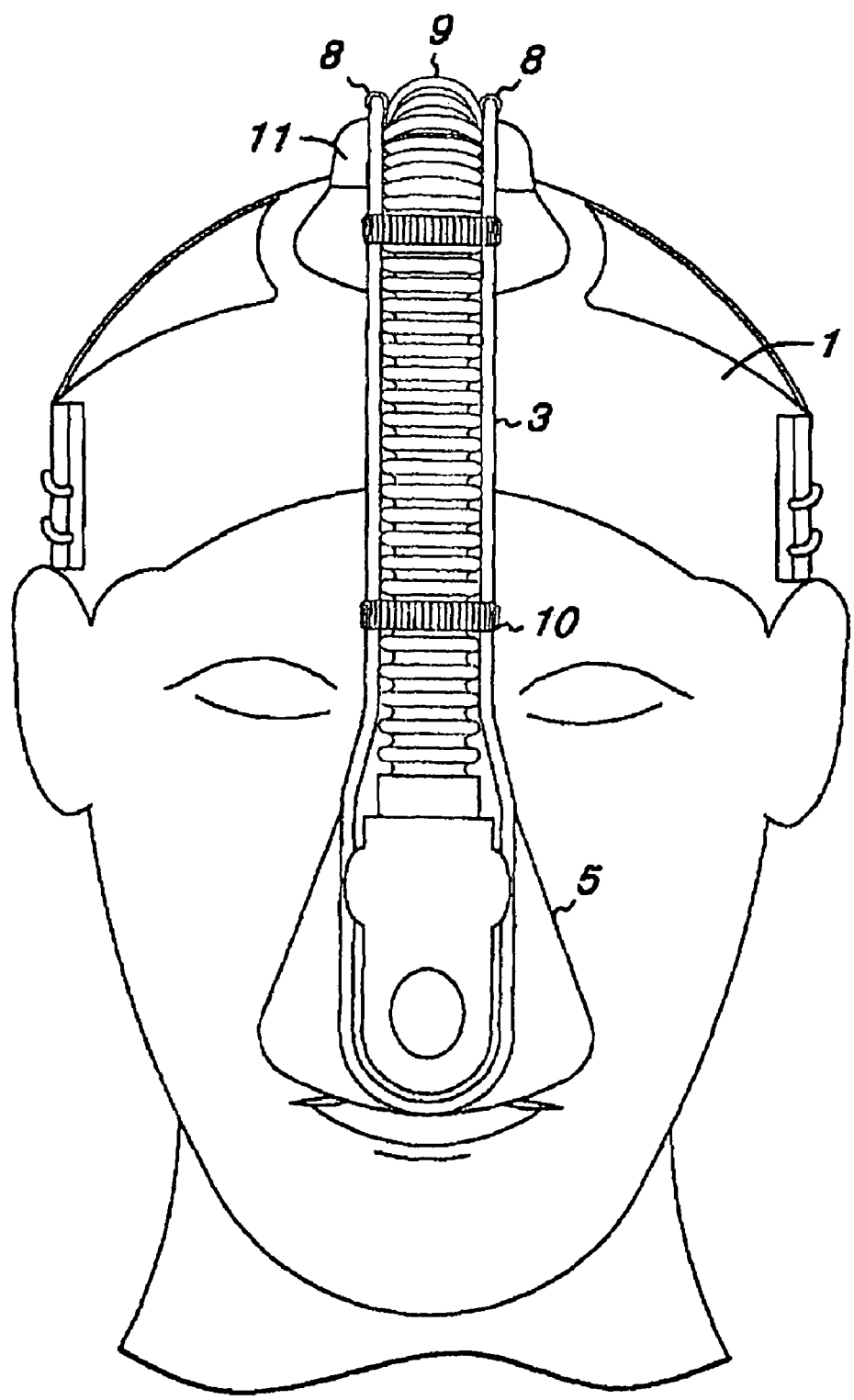
FIG. 3 shows a frontal view of the mask support of the invention.

Looking at FIG. 3, the frontal view of the mask support, the loop of the biasing means is shown to fit around the distal surface of the face mask 5. The adjustment 8 for the biasing means 3 may be a ratchet or a friction fitting. The air tube 9 passes through the groove formed by the loop of the biasing means. The air tube 9 may be secured to the biasing means at 10, the biasing means support at 11 or the medial band. Depending on the preference of the patient, the air tube may be free to swivel at any point, although most patients prefer to use the attchment 10 at the biasing means support to limit movement of the air tube.

Figure 4:
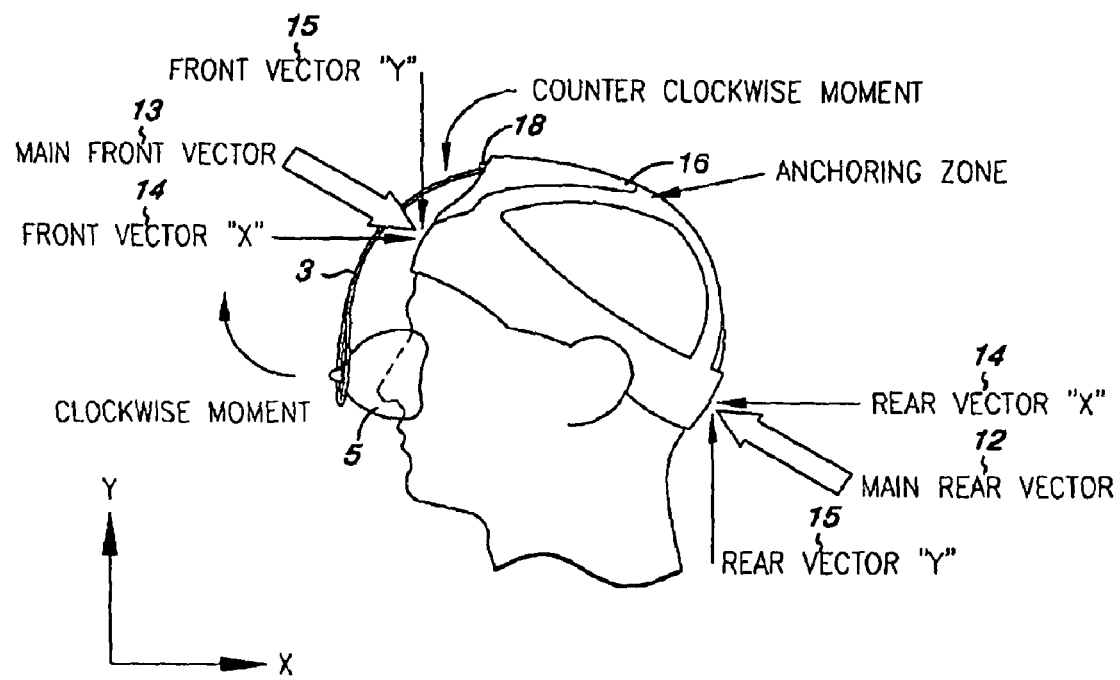
FIG. 4 shows the force vectors of the preferred embodiment of the mask support of the invention.

FIG. 4 shows the force distribution when the mask support, attached to a face mask 3 and blower system, is applied to a head, with the force necessary to hold the face mask apposed to the face. The force is transmitted from the top of the head to the face mask via the biasing means 3. It should be noted that the force will vary from patient to patient. The variables include:

higher or lower positive air pressure to hold the patient's airway open;

to provide adequate flow to a patient requiring breathing assistance;

a more restless patient who tends to dislodge the nosepiece;

to accommodate a patient's personal preference.

or an unusual topology of the patient's face. The biasing force may be increased or decreased by shortening or lengthening each arm of the biasing means at 8.

As noted, the loading of the circumferential band is applied independently of the loading for the face mask. The vectors created in tightening the band include the main rear vector 12 and the main front vector 13, which each occur normal to the surface of the head. The analysis of the resultant X 14 and Y 15 vectors show how the "clamping" of the head is accomplished. Noting the vectors X and Y, it can be seen that as the circumferential edge contacts the forehead at too high a position, clamping would fail because there would be no effective "undercut" for gripping and front vector X would be free to move the non rigid band back off of the head. Likewise, if the band contacts too high on the inion protrusion, rear vector Y would have no undercut to resist it and the flexible band would slip upward off of the head. Once the cap is sufficiently clamped by proper positioning of the hemispheric contour, the medial band is held on the medial line of the head and forms a stable anchor zone 16 for attachment of the biasing means support. The extensive stability of the anchoring zone established by the medial band allows for the use of a short length of rigid or semirigid material comprising the biasing means support. It should be noted that the biasing means support and the biasing means are the only components of the mask support that are not soft and flexible.

With this flexible but stable construction, the biasing means is capable of creating a counter-clockwise moment needed to keep the mask apposed to the face, which translates the force into a clockwise moment of the mask loading force, tending to keep the mask on the face without leaking and without the loading force being applied to a small anchor area.

In use, the patient adjusts the cap by means of the adjustment means 6 to a "loose comfort" and place the cap on his or her head, positioning it from the nape of the neck to the forehead. The patient then uses the quick-sizing cord 7 (on those embodiments which are provided with a quick-sizing means) to pull the cap snugly around the head. The medial bands are adjusted for proper fitting. The cap being fitted, the air tube from a blower is attached to a face mask so that the loop of the biasing means passes around the distal protuberance of the face mask. The ends of the biasing are fitted into the slot of the biasing means support and length 1 adjusted to accommodate variations in bias force required to hold the nose piece apposed to the patient's face. Once the original adjustments are made, the biasing means is left attached to the mask support. The mask support is totally soft and flexible except for the biasing means and the biasing means support, which rests on the patient's head from the upper forehead to the top of the cranium, which are areas less sensitive to pressure than the lower forehead and eye area. The result is a CPAP apparatus which is comfortable, stable and leads to increased patient compliance.

EXAMPLE 2

Second Embodiment

The face mask support of Example 1 is comfortable and stable. Improvements to the design were sought to further reduce the weight and the area of contact with the patient's head to make a support that is even more comfortable, while retaining the clamping feature that provides stability shown in FIG. 4.

Figure 5:
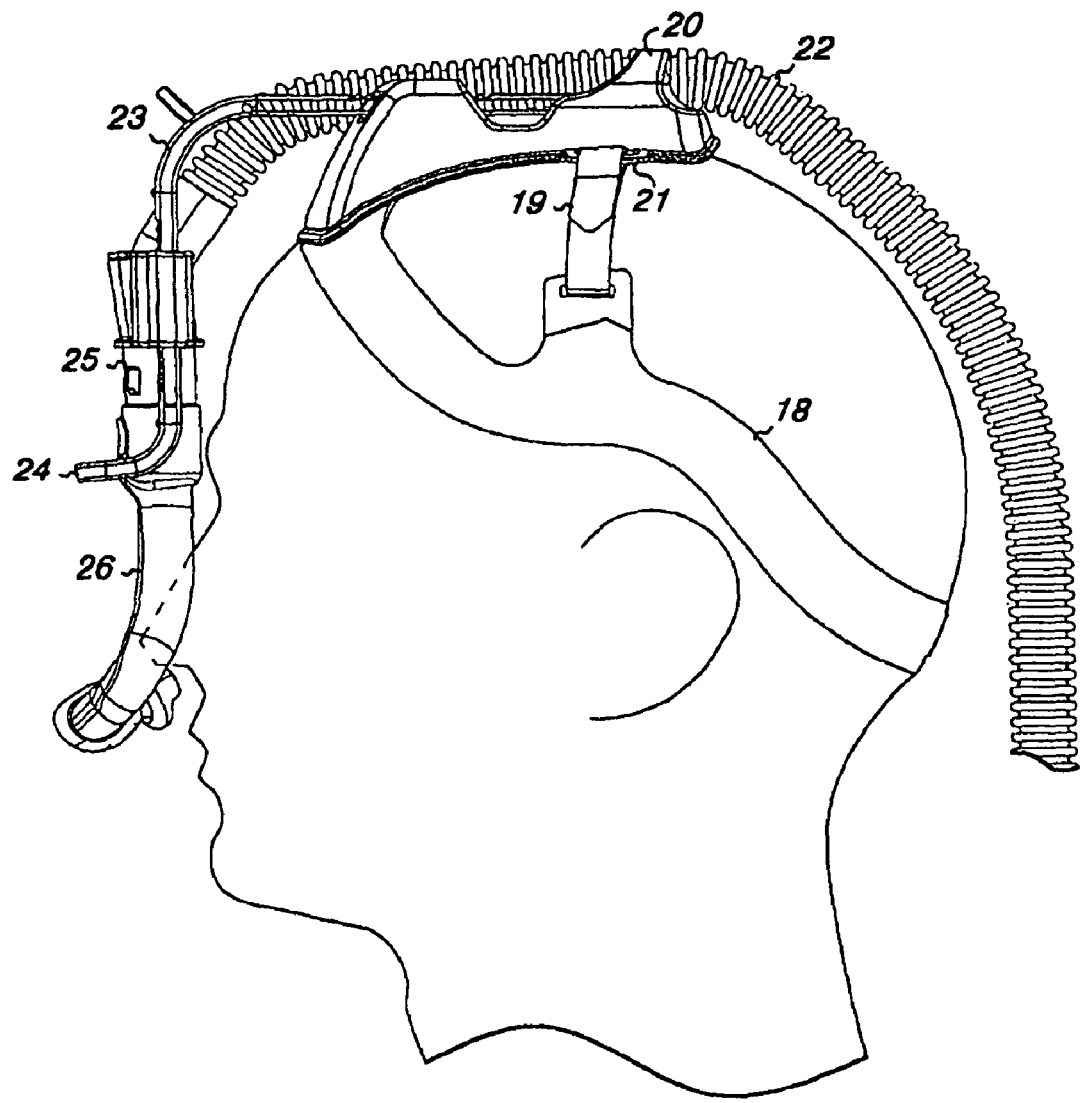
FIG. 5 shows a profile view of the mask support of the invention, fitted with a nasal mask.

FIG. 5 shows a profile view of the invention with the circumferential band 18 encircling the head from the forehead just below the hair line to the inion protrusion of the occipital bone of a patient. The circumferential band in this embodiment is designed to sit higher on the forehead of the patient than in the first embodiment, causing the band to pass near on the ear. Therefore, an S-shaped curve at approximately the level of the ear prevents irritating contact with the ear. A stabilizing band 19 extends upward from approximately the area of the S-shaped curve to the crown of the head. A biasing means support 20 is positioned to extend from the circumferential band to the stabilizing band. The biasing means support may rest on a cushion 21. An airway tubing 22 extends along the top surface of the biasing means support and thence down along the biasing means 23 to loop 24 around the plenum 25 and the nasal mask 26. In this preferred embodiment, a plenum for receiving and venting air is positioned on the biasing means and the loop of the biasing means passes around the plenum, rather than around the nasal mask assembly. This affords sufficient apposing force because the preferred nasal mask is lightly anchored in the nares of the patient and is light in weight.

Figure 6:
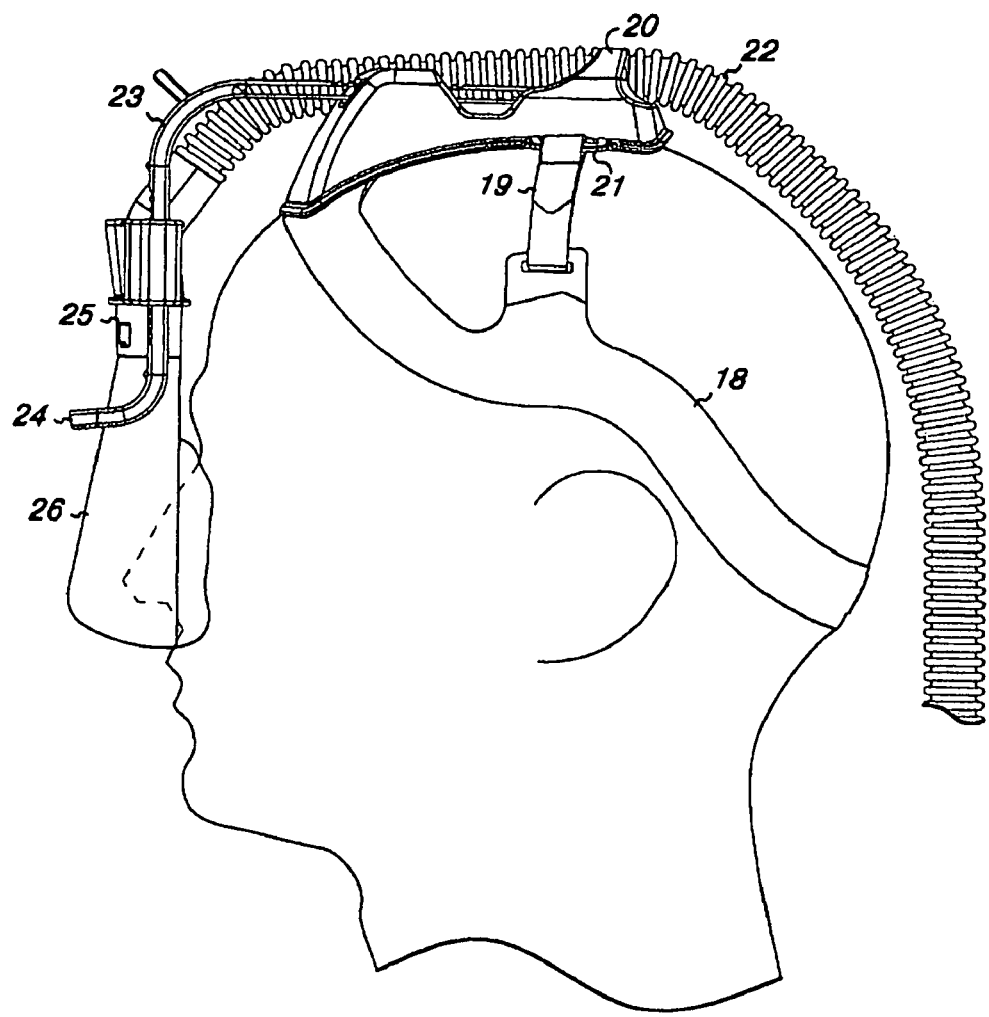
FIG. 6 shows a profile view of the mask support of the invention fitted with a face mask.

FIG. 6 shows a side view of the invention with the circumferential band 18 encircling the head from the forehead to the inion protrusion of the occipital bone of a patient. An S-shaped curve at approximately the level of the ear prevents irritating contact with the ear. A stabilizing band 19 extends upward from approximately the area of the S-shaped curve to the crown of the head. A biasing means support 20 is positioned to extend from the circumferential band to the stabilizing band. The biasing means support may rest on a cushion 21. An airway tubing 22 extends along the top surface of the biasing means support and thence down along the biasing means 23 to loop 24 around the plenum 25 and the face mask 26. In this embodiment, a plenum for receiving and venting air may be positioned on the biasing means and the loop of the biasing means passes around mask assembly. This affords more apposing force than the assembly used with the preferred nasal mask because the larger and heavier face mask requires more apposing force to hold it in place.

Figure 7:
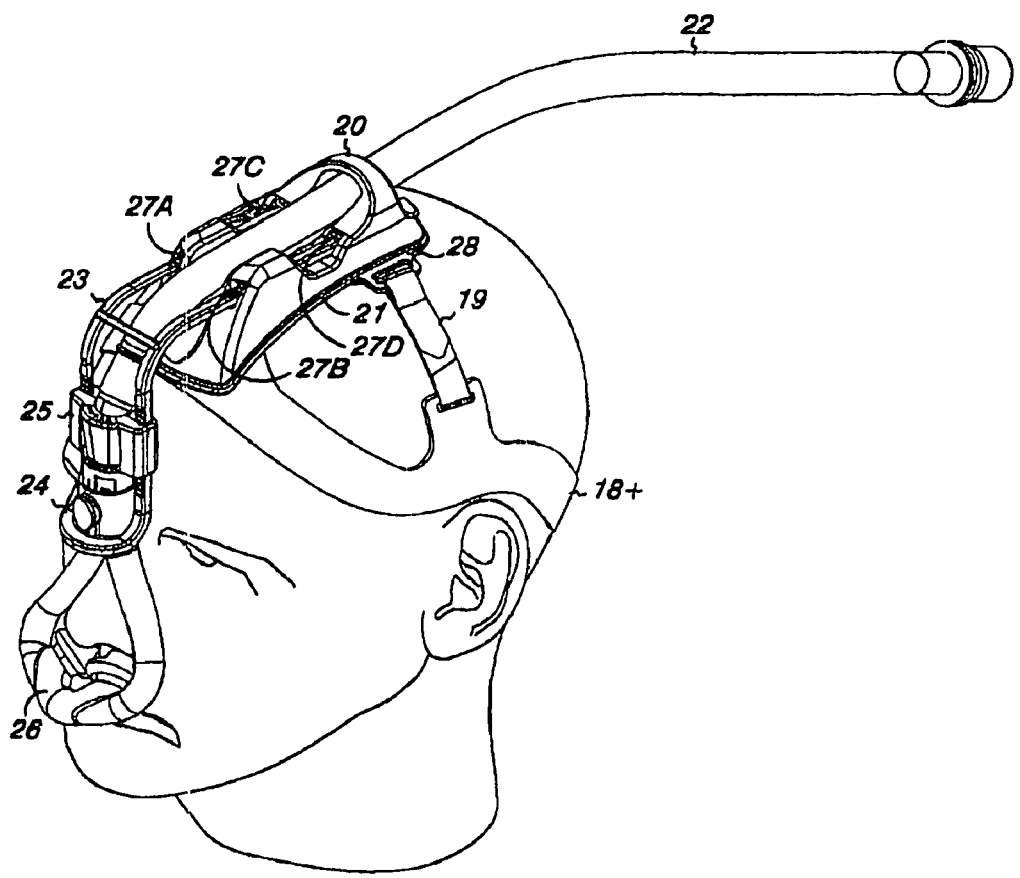
FIG. 7 shows a top view of the invention, fitted with a nasal mask and having a biasing means support cushion.

FIG. 7 shows a top view of the invention with the circumferential band 18 encircling the head from the forehead just below the hairline to the inion protrusion of the occipital bone of a patient. An S-shaped curve at approximately the level of the ear prevents irritating contact with the ear. A stabilizing band 19 is attached to and extends upward from the circumferential band at approximately the area of the S-shaped curve to the crown of the head. A biasing means support 21 is positioned to extend from the circumferential band to the stabilizing band and is attached to the stabilizing band through an attachment 28 on each side of the biasing means support. The biasing means support may rest on a cushion 21 and is provided with receiving slots 27A and 27B. An airway tubing 22 extends along the top surface of the biasing means support and thence down along the biasing means 23 to loop 24 around the plenum 25 above the nasal mask 26. In this preferred embodiment, a plenum for receiving and venting air is positioned on the biasing means and the loop of the biasing means passes around the plenum, rather than around the nasal mask assembly.

Figure 8A:
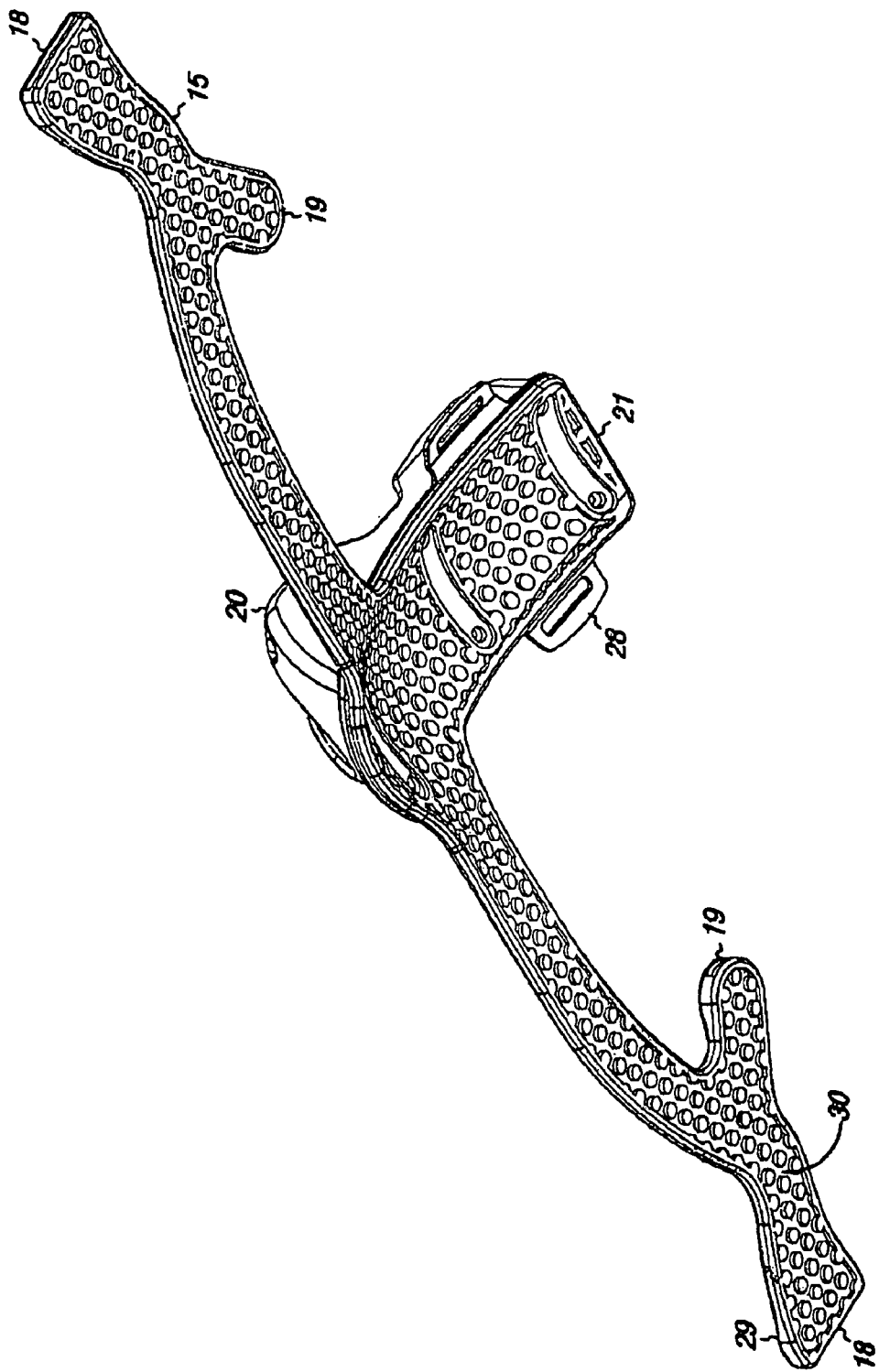
FIG. 8A shows an under side view.
Figure 8B:
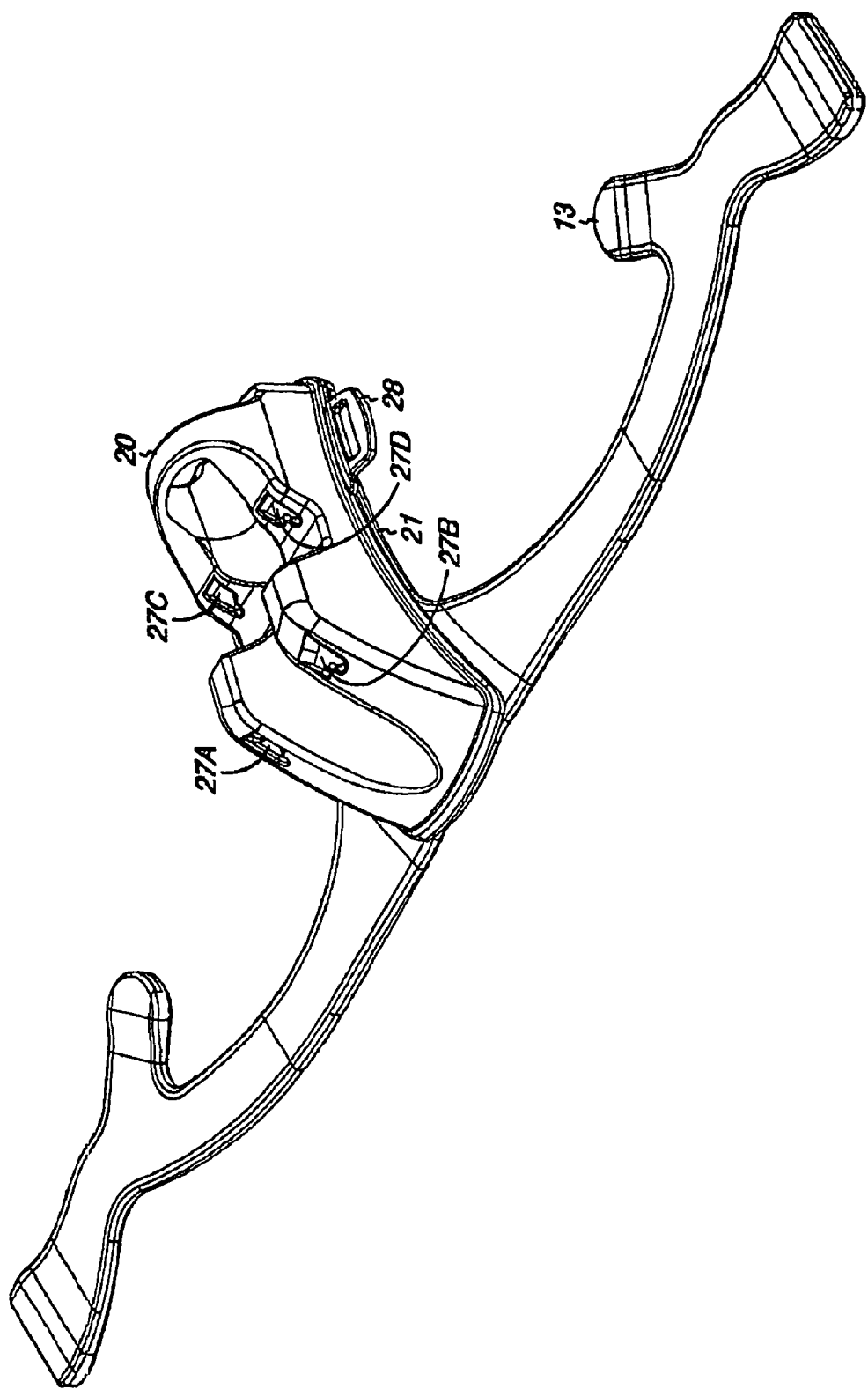
FIG. 8B shows a top view.

FIG. 8A shows the expanded molded circumferential band with the biasing means support 20 positioned on the circumferential band 18 and on the cushion 21. When assembled, the ends of the circumferential band 18 are attached securely to each other by sonic welding or glue, but preferably are attached through adjustment means, which may be buckles, snaps, or preferably, Velcro. The stabilizing bands 19 are conveniently molded as tongues of the circumferential band 18. The attachments 28 may be formed on either the biasing means support or on the outer substrate of the stabilizing band. Both the circumferential band 18 and the stabilizing bands 19 are formed of an outer substrate 29 that is sufficiently firm to prevent the band from rolling, with an inner substrate of softer material 30 on the side that contacts the skin and/or hair. The band may be formed of any suitable material such as silicone/silicone foam or polyethylene/polyethylene foam. FIG. 8B shows a top view of the molded band, further showing the receiving slots 27A and 27B on the biasing means support 20.

Figure 9A:
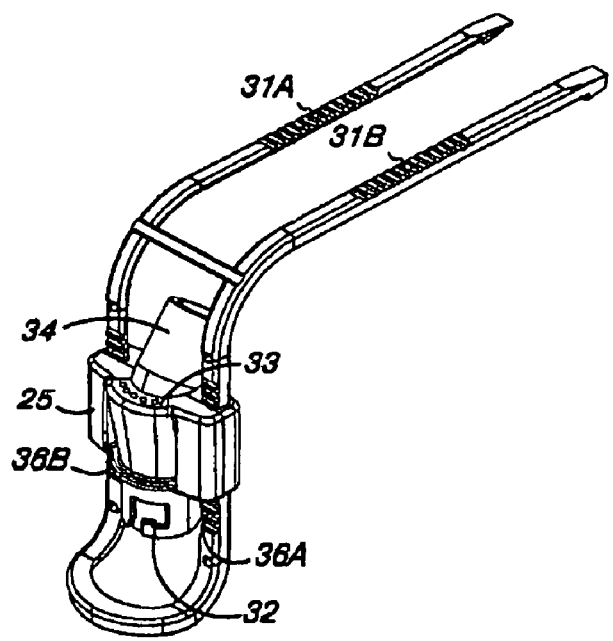
FIG. 9A shows the biasing means with a plenum mounted thereon.

FIG. 9A shows the biasing means 23 with ratchets 31A and 31B, plenum 25 and loop 24 around the plenum. FIG. 5B shows the same, exploded. Ratchets 31A and 31B slide along corresponding ratchets within the biasing means support (not shown) to provide horizontal adjustment. The plenum is attached to the biasing means by springs 33, a tube 34 on the top (shown split) provides connection to the airway tube. A tube 32 connects through the plenum to the connection to a nasal or face mask. Vents 35 are placed on top of the plenum to allow for the expulsion of exhaled air. Ratchets 36 A and 36B on the biasing means slidably correspond to ratchets within the plenum (not shown) to provide vertical adjustment.

Either embodiment of this invention provides the force necessary to hold the nasal or face mask apposed to the face. The force is transmitted from the top of the head to the nasal or face via the biasing means. It should be noted that the force will vary from patient to patient. The variables include:
higher or lower positive air pressure to hold the patient's airway open;
adequate flow to a patient requiring breathing assistance;
a more restless patient who tends to dislodge the mask;
a patient's personal preference; or
an unusual topology of the patient's face.

By providing a lightweight, less restrictive mask support with easily adjustable biasing means, circumferential and stabilizing bands, most patients will find the invention comfortable and will be encouraged to comply with its use.

EXAMPLE 3

Configurations of the Biasing Means

While the configuration of the biasing means as shown in FIGS. 5 to 9 is ideal, the biasing means may be varied. FIG. 10 shows a biasing means 23 with two descending arms inserting into the receiving slots 27A and 27B on the biasing means support 29. The arms are joined into a single descending arm which inserts into a plenum.

Figure 11:
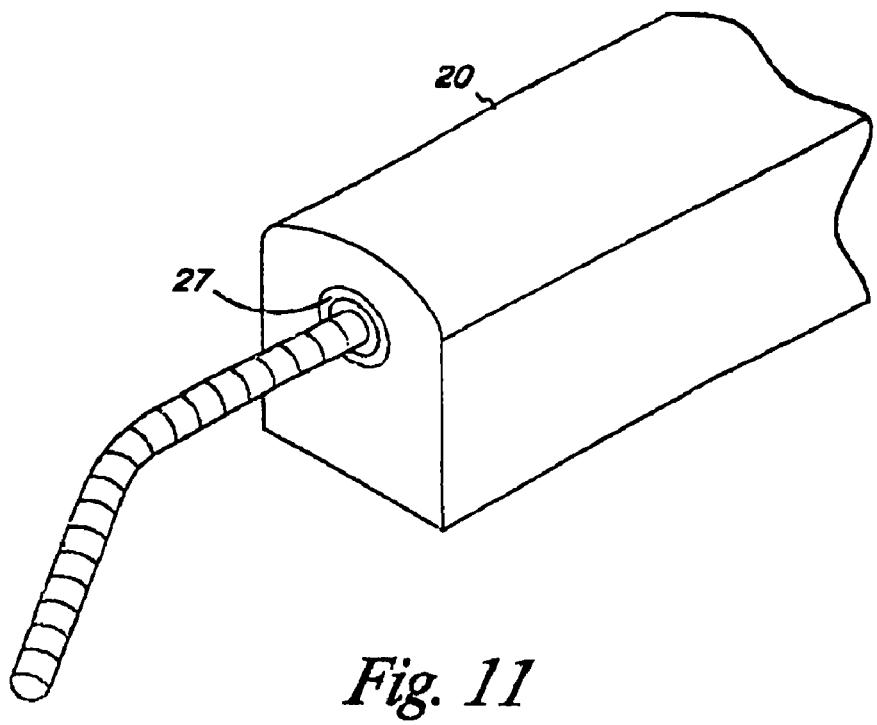
FIG. 11 shows a biasing means support with a receiving slot for a single-armed biasing means.

FIG. 11 shows a biasing means support 20 with a single receiving slot 27 for a single-armed biasing means.

Figure 12:
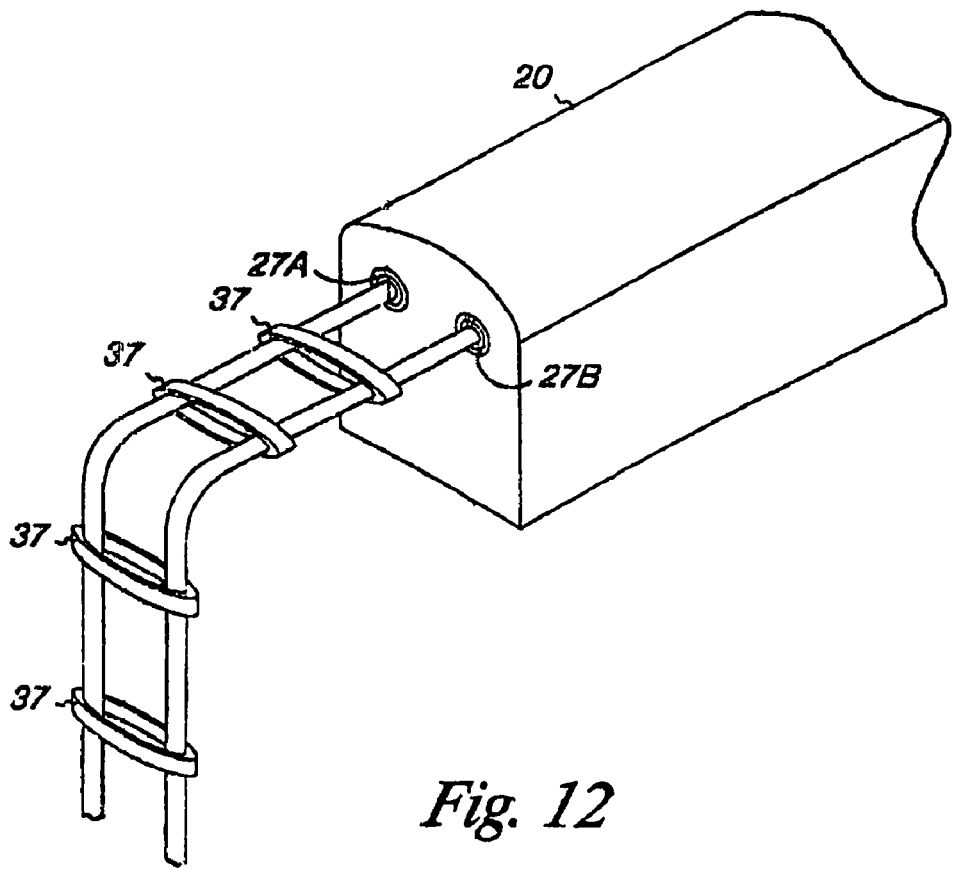
FIG. 12 shows a biasing means secured with bands.

FIG. 12 shows a biasing means inserted through receiving slots 27A and 27B to the biasing means support 20. Each arm is inserted directly into a plenum rather than supporting the plenum by forming a surrounding loop. The bands 37 provide stability.

Figure 13:
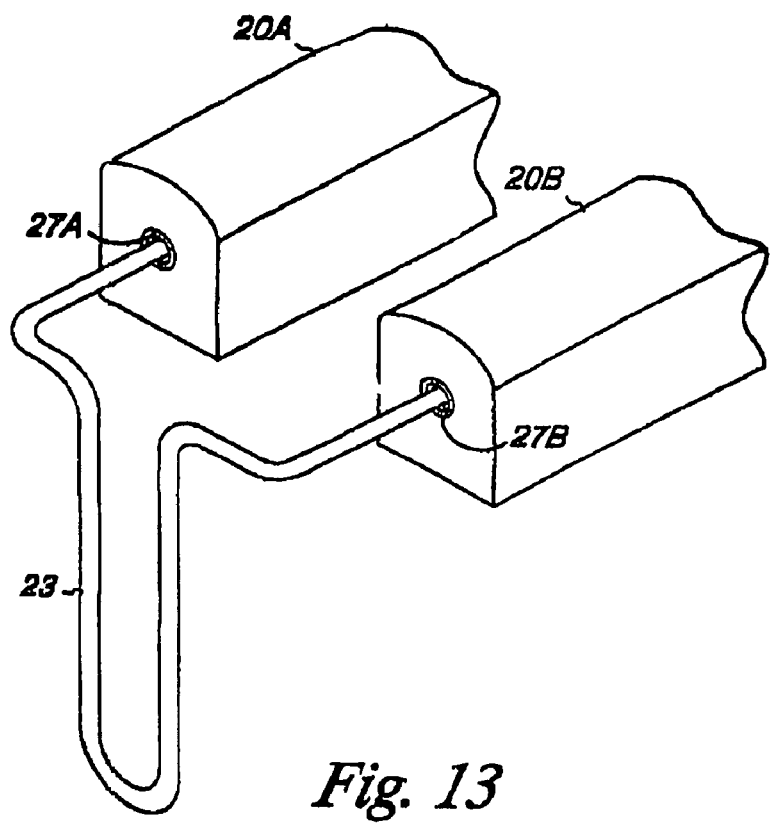
FIG. 13 shows a double biasing means support.

FIG. 13 shows a double biasing means support 20 A and 20B where each arm of the biasing means 23 inserts into a separate biasing means support through receiving slots 27A and 27B.

Figure 14:
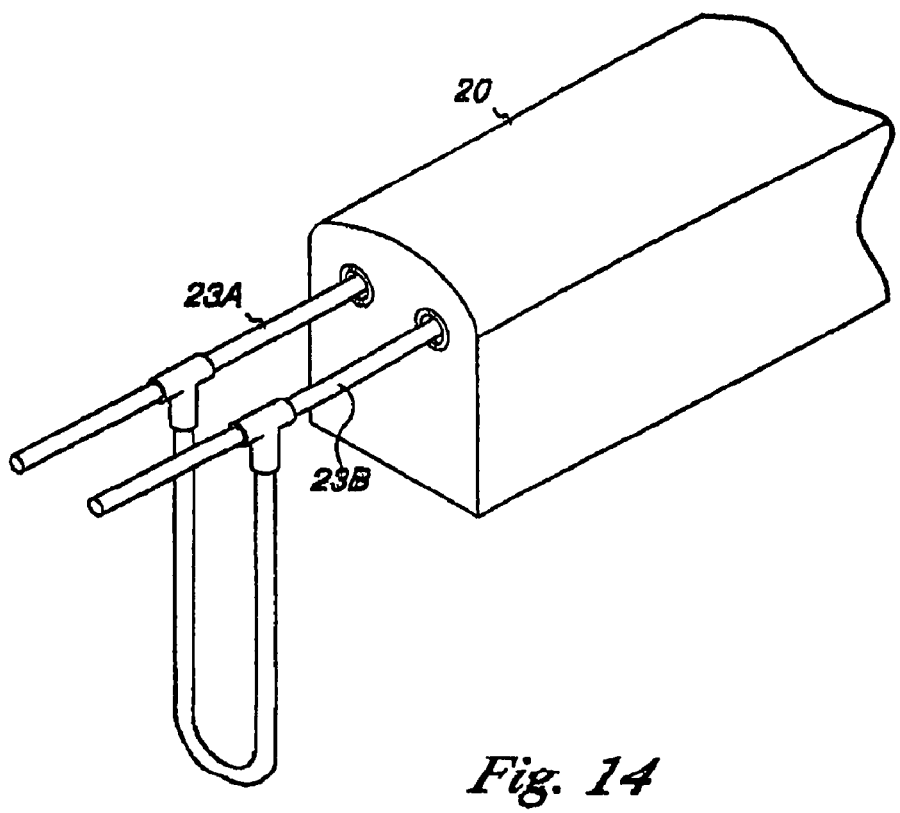
FIG. 14 shows a biasing means comprised of two separate pieces.

FIG. 14 shows a biasing means that is constructed of two separate pieces 23A and 23B.

Figure 9B:
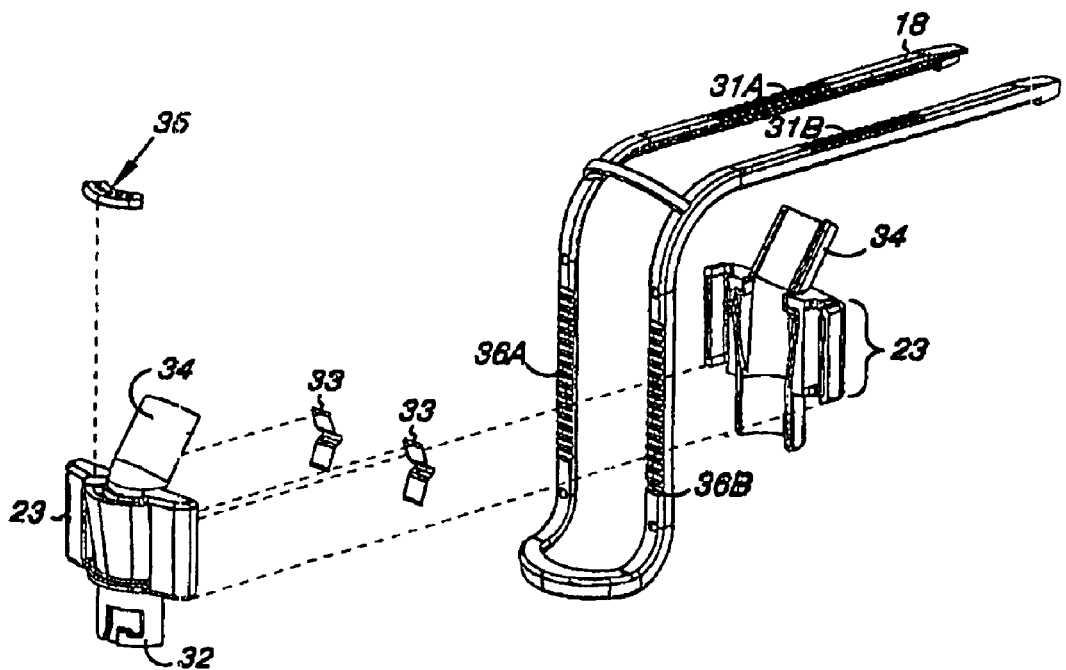
FIG. 9B shows an exploded view of the same.
Figure 10:
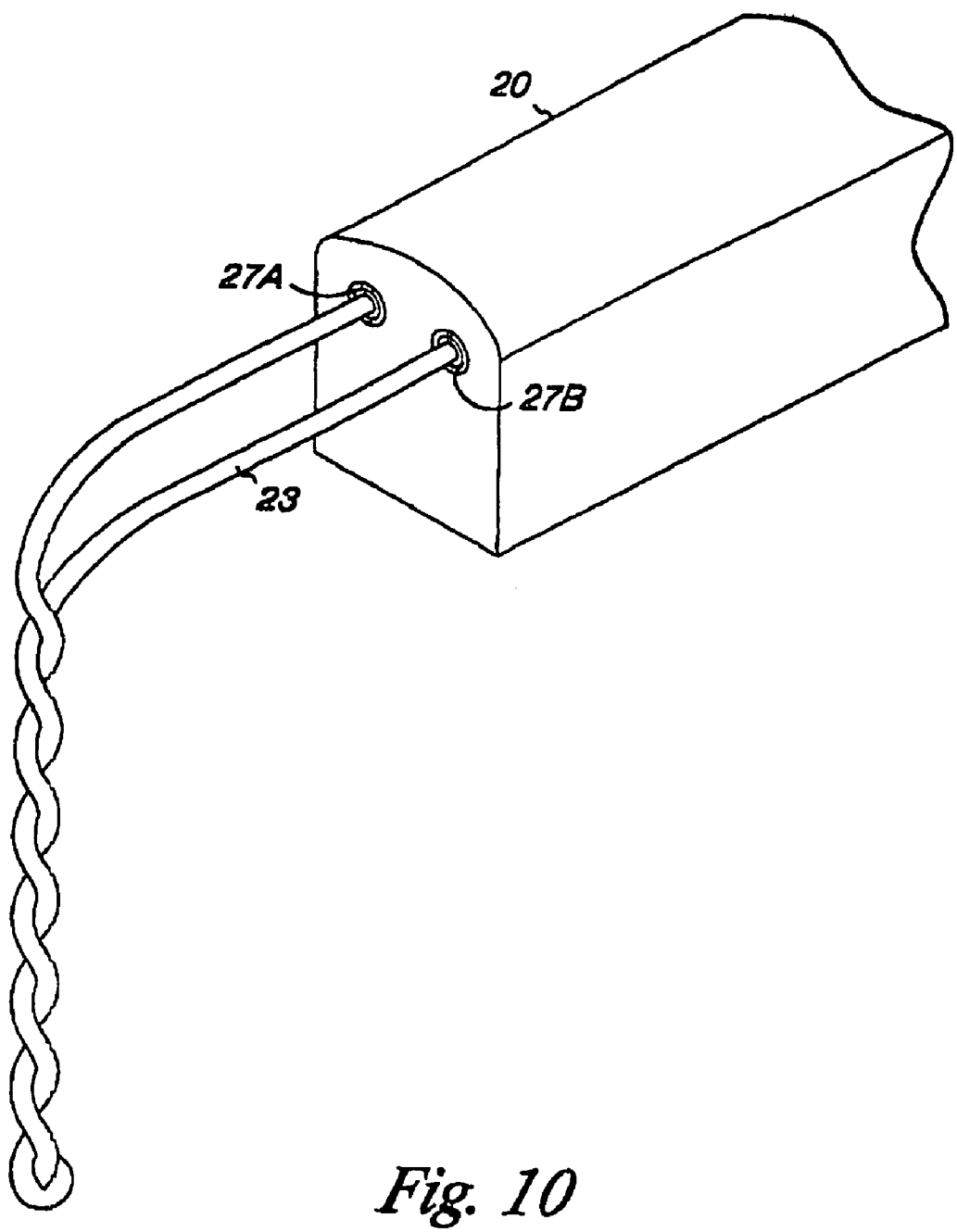
FIG. 10 shows a single insertion of the biasing means into the plenum.

It is to be understood that each of these biasing means as shown in FIGS. 10 through 14 is provided with means for horizontal and vertical adjustment as shown in FIGS. 9A and 9B.

It may be understood that following the teachings of this patent application, those skilled in the art to which it pertains may readily make insubstantial changes, which changes are considered to be within the spirit and scope of this invention.

We claim:

1. A face mask support for a continuous positive airway pressure apparatus, comprising:
a circumferential band adapted to encircle the head of a patient;
at least one stabilizing band attached to the circumferential band; and
a biasing means support, at least a portion of which passes over the medial line of the head and defining a curve to accommodate the curvature of the cranium, the biasing means support secured to the circumferential band at a front end of the biasing means support and secured to the at least one stabilizing band at a back end of the biasing means support, the biasing means support secured to a medial band, the medial band extending over the medial line of the head and secured to the circumferential band and secured to the at least one stabilizing band,
where the front end of the biasing means support is secured to the circumferential band by the medial band and the back end of the biasing means support is secured to the at least one stabilizing band by the medial band.

2. The face mask support of claim 1, wherein a length of the circumferential band is adjustable.

3. The face mask support of claim 1, wherein the circumferential band comprises an elastic material.

4. The face mask support of claim 1, further comprising a biasing means configured to attach to the biasing means support.

5. The face mask support of claim 4, wherein the biasing means comprises descending lateral arms configured to support a face mask.

* * * * *